United States Patent [19]
Whaley

[11] Patent Number: 4,784,846
[45] Date of Patent: Nov. 15, 1988

[54] BROWN MICACEOUS OXIDE FOOT POWDER

[76] Inventor: Dean A. Whaley, 2706 Lafayette Ave., Richmond, Va. 23228

[21] Appl. No.: 49,099

[22] Filed: May 13, 1987

[51] Int. Cl.[4] .......... A61K 7/32; A61K 7/38; A61K 9/14
[52] U.S. Cl. .......... 424/68; 424/69
[58] Field of Search .......... 424/68, 69

[56] References Cited

U.S. PATENT DOCUMENTS

| | | | |
|---|---|---|---|
| 1,558,405 | 10/1925 | Smith | 424/65 |
| 2,033,758 | 3/1936 | Cronan et al. | 424/65 |
| 3,977,888 | 8/1976 | Sano et al. | 106/74 |
| 4,128,630 | 12/1978 | Hayashi et al. | 424/69 |
| 4,337,859 | 7/1982 | Murphy et al. | 206/37 |
| 4,362,715 | 12/1982 | Strianse et al. | 424/78 |
| 4,414,200 | 11/1983 | Murphy et al. | 424/63 |
| 4,572,690 | 2/1986 | Savanuck | 424/69 X |
| 4,603,047 | 7/1986 | Watanabe et al. | 424/63 |

FOREIGN PATENT DOCUMENTS

| | | | |
|---|---|---|---|
| 687474 | 1/1940 | Fed. Rep. of Germany | 424/69 |
| 964091 | 8/1949 | Fed. Rep. of Germany | 424/69 |
| 712971 | 8/1931 | France | 424/69 |
| 0038635 | 4/1978 | Japan | 424/69 |
| 0122306 | 9/1984 | Japan | 424/69 |
| 1158913 | 7/1986 | Japan | 424/69 |
| 284830 | 2/1928 | United Kingdom | 424/69 |

OTHER PUBLICATIONS

The Merck Index, 6th Edition, 1952, pp. 536 and 860.
Janistyn, Riechstolfe Seifen Kosmetika, Band I, pp. 362 to 364.

*Primary Examiner*—Dale R. Ore
*Attorney, Agent, or Firm*—Robert E. Bushnell

[57] ABSTRACT

A composition and process for controlling perspiration and odors on mammalian skin in which an effective amount of a topical composition in the form of a finely divided powder including substantially no water solubles and consisting by weight of from 55% to 45% aluminum oxide, 37% to 25% silicon oxide and 15% to 1% red iron oxide is applied to mammalian skin as needed.

8 Claims, No Drawings

BROWN MICACEOUS OXIDE FOOT POWDER

DESCRIPTION

Technical Field

This invention relates to body treating compositions and, more particularly, to compositions of body powders for absorbing and to method of producing and using such compositions.

BACKGROUND ART

Prior body treatment compositions often resulted in severe drying of mammalian skin with concomitant side effects such as skin cracking, and consequential user discomfort.

STATEMENT OF THE INVENTION

Accordingly, it is an object of the present invention to provide an improved mammalian skin treatment composition.

It is another object to provide an improved foot powder.

It is a further object to provide an efficacious mammalian skin treatment powder exhibiting moisture absorption and deodorant characteritics.

It is still another object to provide a process for topical application of a mammalian skin treatment powder.

It is yet another object to provide a process for producing a composition for controlling perspiration and odors on mammalian skin.

Briefly, the foregoing and other objects are achieved with compositions and processes in which a substance including substantially no water solubles and comprising by weight of from 55% to 45% aluminum oxide, 37% to 25% silicon dioxide and 15% to 1% red iron oxide is screened to reduce the percentage of red iron oxide to less than 5% by weight of the screened material, and the screened material is reduced in a mill to a powder with at least 95% by weight passing through a screen having 325 meshes per inch. The composition may be topically applied to mammalian skin as needed.

DETAILED DESCRIPTION OF THE INVENTION

In accordance with the invention, a naturally occurring red micaceous substance including substantially no water solubles and comprising by weight from 55% to 45% aluminum oxide, 37% to 25% silicon oxide and 15% to 1% red oxide is dried at 450 degrees Fahrenheit. The dried substance is then screened to reduce the percentage of red iron oxide to less than 5% by weight (preferably to 1.5% to 2% by weight). The screened material is reduced in a ball mill until at least 95% (and preferably more than 98%) by weight passes through a screen having 325 meshes per inch.

The resulting composition is in the form of a finely divided powder containing substantially no water solubles.

EXAMPLE I

Analysis of one sample of a brown micaceous substance produced according to the foregoing procedure resulted in the following analysis:

51% $Al_2O_3$
31% Silicon dioxide
14% $Fe_2O_3$
Particle Size: 96% passing through 325 mesh screen Specific Gravity: 2.6–3.7
Water Solubles: Nill
Color: Light brown to tan
Oil Absorption: 54

This matérial performs satisfactorily as a foot powder for perspiration absorption and as a foot deodorant.

EXAMPLE II

Between 1¼ and 1½ of a teaspoon of the composition described in Example I was placed within each shoe of an adult male. Each shoe was vigorously shaken to distribute the powder throughout its interior. Additional powder was rubbed lightly between the toes of an adult male. This procedure was repeated in two or three day intervals, as needed. Examination indicated that the powder efficaceously served as a foot powder with the ability to eliminate undesirable odors such as those associated with perspiring feet. Examination also indicated that side effects were minimal, with no cracking of the skin.

EXAMPLE III

Analysis of another sample of the brown miaceous substance showed the following composition by percentage of weight:

54% $Al_2O_3$
37% Silicon
5% $Fe_2O_3$
2% Mg.

The silicon content is reducible to about 30% by weight through screening.

EXAMPLE IV

Spectrographic analysis of another sample of the brown micaceous substance showed, in addition to aluminum oxide, red iron oxide, and silicon. The substance contained the following values in parts per million, except where noted in percentage by weight, to the nearest number in the series 1, 1.5, 2, 3, 5, 7:

| | |
|---|---|
| Ca | 1% |
| Mg | 1.5% |
| Ag | <1 |
| As | <500 |
| B | 70 |
| Ba | 15 |
| Be | 2 |
| Bi | <10 |
| Cd | <50 |
| Co | <5 |
| Cr | 50 |
| Cu | 10 |
| Ga | <10 |
| Ge | <20 |
| La | <20 |
| Mn | 150 |
| Mo | 2 |
| Nb | <20 |
| Ni | 10 |
| Pb | <10 |
| Sb | <100 |
| Sc | 10 |
| Sn | <10 |
| Sr | <50 |
| Ti | 1,500 |
| V | 50 |
| W | <50 |
| Y | <10 |
| Zn | <200 |
| Zr | 20 |

It is evident that those skilled in the art may now make numerous uses and modifications of any departures from the specific embodiments described herein without departing from the principles of the inventions disclosed. Consequently, the inventions are to be construed as embracing each and every novel feature and novel combination of features present in or possessed by the composition and processes herein disclosed and limited only by the spirit and scope of the appended claims.

What is claimed is:

1. A topical composition for application to mammalian skin, comprising by weight of from 55% to 45% aluminum oxide about 30% silicon oxide, and 5% to 1% red iron oxide, and including substantially no water solubles.

2. The topical composition of claim 1, wherein the composition is a finely divided powder.

3. The composition of claim 1, comprising from 1.5% to 2% by weight of red iron oxide.

4. A process for controlling perspiration and odors on mammalian skin, comprising the application to mammalian skin at the locale of moisture of an effective amount of a composition in the form of a finely divided powder including substantially no water solubles and consisting by weight of from 55% to 45% aluminum oxide, 37% to 25% silicon oxide, and 15% to 1% red iron oxide.

5. The process of claim 4, wherein the composition comprises less than 5% by weight of red iron oxide.

6. The process of claim 4, wherein the composition comprises from 1.5% to 2% by weight of red iron oxide.

7. A process for producing a composition for controlling perspiration on mammalian skin, comprising:

drying a substance including substantially no water solubles and comprising by weight of from 55% to 45% aluminum oxide, 37% to 25% silicon oxide, and 15% to 1% red iron oxide;

screening the substance to reduce the percentage of red iron oxide to less than 5% by weight of screened material; and reducing the screened material in a mill to a powder with at least 95% by weight of the screened material passing through a screen having 325 meshes per inch.

8. The process of claim 7, wherein the composition comprises from 1.5% to 2% by weight of red iron oxide.

* * * * *